United States Patent [19]
Ruse

[11] Patent Number: 5,242,836
[45] Date of Patent: Sep. 7, 1993

[54] METHOD AND DEVICE FOR THE TREATMENT OF A GAS TO BE ANALYZED

[75] Inventor: Alois Ruse, Oberursel, Fed. Rep. of Germany

[73] Assignee: Hartmann & Braun Aktiengesellschaft, Frankfurt, Fed. Rep. of Germany

[21] Appl. No.: 878,663

[22] Filed: May 4, 1992

[30] Foreign Application Priority Data

May 3, 1991 [DE] Fed. Rep. of Germany ....... 4114468

[51] Int. Cl.$^5$ .......................... G01N 1/18; G01N 7/00; G01N 30/96
[52] U.S. Cl. ...................................... 436/178; 422/83; 422/88; 422/101; 73/23.2
[58] Field of Search .................. 436/177, 178; 422/83, 422/101, 88; 73/23.2

[56] References Cited

U.S. PATENT DOCUMENTS

| | | | |
|---|---|---|---|
| 1,522,848 | 1/1925 | Voress et al. | 436/178 |
| 4,479,379 | 10/1984 | Tarcy | 73/23 |
| 4,764,344 | 8/1988 | Knab | 422/89 |

*Primary Examiner*—James C. Housel
*Assistant Examiner*—N. Bhat
*Attorney, Agent, or Firm*—Horst M. Kasper

[57] ABSTRACT

A method and a device for the treatment of a gas to be analyzed in a gas mixture, including a separation of components from the gas mixture, where the presence of said components is undesirable for performing the analysis. An aerosol filter is employed for the separation of undesired components. A reagent material is admixed to the gas stream, wherein the reagent material forms an aerosol together with the undesired components of the gas mixture. The gas stream passes a reaction path (4) after the entering of the reagent materials. The reaction distance (4) provides a dwelling time for the generation of aerosols in the mixture of gases and the reagent material. The aerosol filter (5) is disposed downstream of the reaction distance (4), which separates the aerosols from the gas stream.

18 Claims, 2 Drawing Sheets

METHOD AND DEVICE FOR THE TREATMENT OF A GAS TO BE ANALYZED

BACKGROUND OF THE INVENTION

1. Field of the Invention

The invention relates to a method for the treatment of a gas to be analyzed contained in a gas mixture and to a device for the performance of this method.

2. Brief Description of the Background of the Invention Including Prior Art

A method for the treatment of a gas to be analyzed is known from the German Patent DE-PS-3,716,350, where a water vapor, contained in a gas stream, and other vaporous materials are deposited by cooling below the respective dew point. In order to relieve the gas to be analyzed completely from water, the water present as an aerosol is removed by an aerosol filter, where the aerosol filter contains a fiber material accepting and absorbing the humidity. Further undesired components in the gas stream such as, for example, sulfur trioxide $SO_3$, halogenides or the like are removed by chemical reactions in sacrificial metal filters.

A method and a device for the deposition of aerosols in flowing gases is known from the German Printed Patent Document DE-OS-3,638,096, where the gases are subjected in a first stage to a frequent deflection of their movement direction, such that the colloids of the dispersion are combined to drops, said drops are separated based on their gravity and pass in a second stage over an adsorption distance, which is effective adsorptively and desorptively. A filter packing to be passed by the gas loaded with the aerosols is disposed in a casing of the device, and a chamber is furnished for the reception of a filler material, acting on the aerosol in an adsorptive and desorptive way.

A method for the determination of sulfur trioxide is described in the Patent of the German Democratic Republic DD 75,828, wherein a sample gas stream is subdivided into two congruent partial streams. A partial stream flows through a contact pipe, heated to at least 900° C., and the second partial stream is passed through a cooling pipe after mixing with water vapors. The sulfur dioxide contents of the two partial streams are measured and the content in sulfur trioxide is determined by forming the difference of the two measurement values.

SUMMARY OF THE INVENTION

1. Purposes of the Invention

It is an object of the present invention to furnish a method of gas treatment, which allows with small apparatus expenditures to separate a gas to be analyzed from substances which interfere in the analysis without a requirement of performing chemical reactions.

It is another object of the present invention to eliminate a sulfur trioxide from gas compositions to be analyzed.

It is yet a further object of the present invention to separate tar from a gas stream to be analyzed.

These and other objects and advantages of the present invention will become evident from the description which follows.

2. Brief Description of the Invention

According to the present invention there is provided for a method for treatment of a gas mixture to be analyzed. The gas mixture is sampled to provide a gas stream. An additional reagent is mixed to the gas stream. The reagent forms with undesired components an aerosol. The gas stream after admixing of the reagent passes through a reaction tube. The reaction tube provides a dwelling time sufficient for a generation of aerosols incorporating said undesired components. Components of the gas mixture, undesirable for an analytical procedure, are separated from the gas mixture with an aerosol filter.

The reagent material can be continuously metered by feeding the reagent material through a metering device into the gas stream. The reagent material can be metered under cyclically feeding of the reagent material through a metering device into the gas stream.

Water can be employed as the reagent material for an elimination of sulfur trioxide $SO_3$ from the gas stream. The weight parts of water to weight parts of sulfur trioxide $SO_3$ can be metered in a ratio of larger than 20 to 1.

Solvents for tars can be employed as reaction material for an elimination of tars from the gas stream.

The separation of the aerosol particles can be performed in a phase separator connected to the aerosol filter.

The gas stream after separating the aerosol particles can be suctioned into a gas analyzer. The gas stream can be analyzed in the gas analyzer.

The present invention further provides for an apparatus for the treatment of a gas to be analyzed. A feed-in port for entering a gas sample stream including undesired components to be separated from the gas sample stream allows performing a gas analysis of the gas sample stream. Means are connected to the feed-in port for adding reagent material to the gas sample stream. A reaction tube has an input end and an output end and is connected to the feed-in port. The gas stream passes through the reaction tube over a reaction distance after feeding in of the reagent material for providing a dwelling time for a generation of aerosols with the undesired components in the mixture of the gas sample stream and of the reagent material. An aerosol filter has an input connected to the output of the reaction tube and has an output. The aerosol filter is disposed downstream of the reaction tube. The aerosol filter separates the aerosols from the gas stream.

A discharge port can be disposed at the aerosol filter. The discharge port can allow the use of the aerosol filter as a phase separator.

A phase separator can have an input connected to the output of the aerosol filter and can have an output.

A suction pump can have an intake connected to the output of the phase separator and can have an output. A gas analyzer can have an input connected to the output of the suction pump.

The invention employs the feature that a plurality of gases, accompanying the gas stream, are forming spontaneously fogs, mists or aerosols with certain materials. For example, sulfur trioxide $SO_3$, hydrogen chloride HCl, silanes, and chlorosilane belong to these gases. The reagents can be liquid or gaseous materials. Water can be fed into the gas stream as a reagent material in the case of sulfur trioxide $SO_3$, or hydrogen chloride HCl. If a solvent for tars is added to the gas stream, then the aerosols forming from the tar droplets can be deposited in the aerosol filter, without the tar becoming solidified or resinous in the filter. The treatment of the gas with a solvent has proven to be useful in case of wood distillation gas and wood carbonization gas, such as is employed for the smoking and curing of meat products.

The mixture of the gases to be separated and of the added reagent material requires a certain dwelling time, such that the reagent can evaporate and can form the largest possible droplets with the respective gases. These droplets are deposited after passage of a predetermined reaction distance in a commercially available aerosol filter. The gases, the aerosols and the residual reagent material enter in the same flow direction into the aerosol filter and flow through the pores of the filter. A pore narrowing occurs based on the wetting of the filter pores with the aerosols and possibly the liquid reagent material and the deposition degree of the filter increases.

The filter casing is filled with the deposited liquid. A rewash effect is thereby generated and the dwelling time of the gas to be analyzed is shortened. The mixture of the gas, of the deposited aerosols and of the excessive reagent material discharges from the aerosol filter. The gas to be analyzed is separated from the liquid in a phase separator connected downstream of the aerosol filter and is fed with the aid of a delivery unit for gas to be tested to the analyzer.

The aerosol filter itself can also be employed as a phase separator, in cases where the resulting poorer time behavior of the filtering does not present a problem.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

In the accompanying drawings, in which are shown several of the various possible embodiments of the present invention.

DESCRIPTION OF INVENTION AND PREFERRED EMBODIMENT

Figure 1:
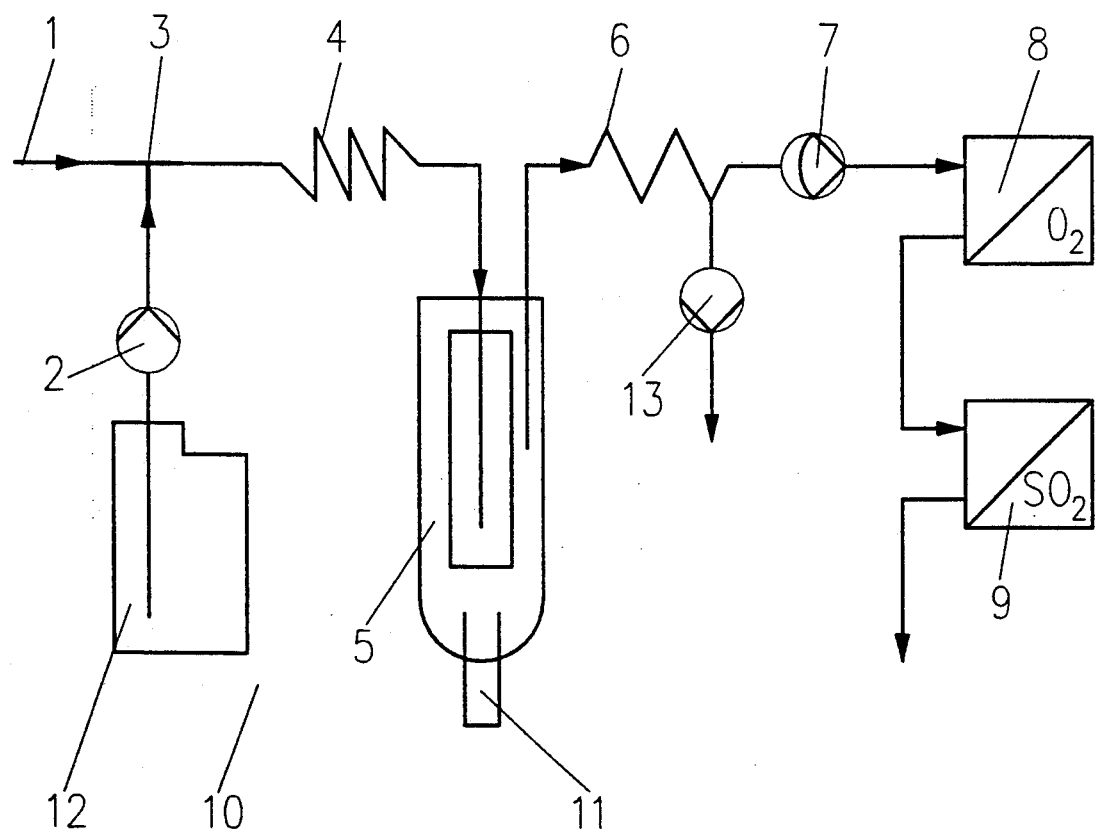
FIG. 1 shows a schematic diagram illustrating the method of a gas treatment.

According to the present invention there is provided for a method for treatment of a gas to be analyzed contained in a gas mixture. Components of the gas mixture, undesirable for an analytical procedure, are separated from the gas mixture under use of an aerosol filter. A reagent is mixed to the gas stream. The reagent forms with the undesired components an aerosol. The gas stream flows after admixing the reagent through a reaction path distance. The reaction path distance provides a dwelling time for the generation of aerosols.

The reagent material 3 can be continuously fed through a metering device 10 into the gas stream. The reagent material can be cyclically fed to the gas stream through a metering device 10.

Water can be employed as the reagent material for an elimination of sulfur trioxide $SO_3$ from the gas stream. The weight parts of water to weight parts of sulfur trioxide $SO_3$ can be metered in a ratio of larger than 20 to 1.

Solvents for tars can be employed as reaction material for an elimination of tars from the gas stream.

An apparatus is provided for the treatment of a gas to be analyzed in a gas mixture, in particular where undesired components are to be separated from the gas mixture for performing an analysis. A feed-in port is provided for entering a gas sample stream. Means are connected to the feed-in port for adding reagent material to the gas sample stream. A reaction tube has an input end and an output end and is connected to the feed-in port. The gas stream passes through the reaction tube 4 over a reaction distance after feeding in the reagent material 3, for providing a dwelling time for a generation of aerosols with the undesired components in the mixture of the gas sample stream and of the reagent material. An aerosol filter 5 has an input connected to the output of the reaction tube and an output. The aerosol filter 5 is disposed downstream of the reaction tube 4. The aerosol filter 5 separates the aerosols from the gas stream.

The aerosol filter 5 can be furnished with a discharge port 11. The discharge port 11 can allow the use the aerosol filter 5 as a phase separator.

FIG. 1 shows schematically the plan for the gas flow of a device for the treatment of oxygen $O_2$ and sulfur dioxide $SO_2$ in a gas mixture. Sulfur trioxide $SO_3$ is removed from said gas mixture as an undesired component by mixing water as a reagent material in about a ratio of more than 20 weight parts of water to one weight part of sulfur trioxide $SO_3$. Preferably, the weight parts of water are from at least 30 to 50 times relative to a maximum expected weight part value of sulfur trioxide $SO_3$ in the gas stream.

The adding and mixing of the reagent such as water is taught in the German Patent 2,105,307 to W. Reichel et al. and in the corresponding U.S. Pat. No. 3,698,868. The reference teaches a liquid dispenser for feeding of reagents to an automatically operating apparatus for a continuous analysis of samples. U.S. Pat. No. 3,698,868 further refers to U.S. Pat. No. 2,879,141. These references teach that the liquid be transported with suction or pressure pumps.

The device comprises a metering device 10 for the addition of water, a reaction distance 4, an aerosol filter 5 disposed in the gas stream, a phase separator 6, and two analyzers 8 and 9 for the determination of the gas concentration. Gas conveying systems are described in Listenblatt 23-1.41 published by Mannesmann Hartmann & Braun, Frankfurt am Main, Federal Republic of Germany.

Figure 2:
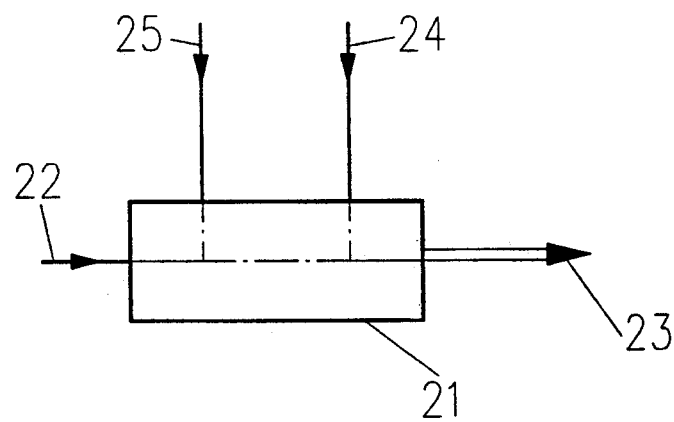
FIG. 2 shows a schematic diagram of a T-connection and a washer of a gas stream.

The gas mixture to be treated enters into the gas line at 1 or it is suctioned from the gas line by the suction pump 7. The metering device 10 mixes with the aid of a metering pump 2 a predetermined amount of reaction agent water from a vessel 12 at the T-connection 3 into the gas mixture coming from line 1 and passing-by at the T-connection 3. The T-connection 3 can be provided by a gas distributor piece 21 shown in FIG. 2. The gas distributor piece 21 includes a first input 22, a second input 24, a third input 25, and an output 23. The third input 23 is not required in the context of the present invention. The connection hose at the first input 22 can be a viton tube with a diameter of 4 mm and a 1 mm wall thickness. The second input and the output can be connected to a plastic tubing made of polytetrafluoroethylene PTFE having an inner diameter of 2 mm and having a wall thickness of 0.5 mm.

A reaction distance pipe 4 is passed by the gas mixture, wherein the sulfur trioxide $SO_3$/water $H_2O$ mixture forms an aerosol, including droplets of sulfuric acid and associated bound water. Preferably, turbulences are introduced into the gas mixture while in the reaction distance pipe. The length of the reaction path can be up to a maximum of about 0.5 meters and is preferably not longer than 30 centimeters. The inner diameter of the reaction path tube can be from about 0.1 to 2 mm and is preferably from about 0.2 to 0.8 mm. The reaction path is made of a capillary tubing made of a corrosion resistant material such as a plastic material made of polytetrafluoroethylen PTFE. The remaining gas lines employed can have an inner diameter of from about 1 mm through 10 mm and of preferably from about 2 through 6 mm.

The length of the reaction path depends on the interfering component present in the gas to be analyzed. For example, in case of a presence of an interfering component of sulfur dioxide or sulfur trioxide, the reaction path length can be from about 30 to 50 cm. On the other hand, where the interfering component is hydrogen chloride HCl, then the length of the reaction path can be from about 0 to 50 mm and is preferably from about 5 to 20 mm. In case of an interfering component of hydrogen chloride HCl, the dwelling time in the aerosol filter 5 will be sufficient and no reaction path is required.

The reaction of the reagent with the interfering component can be performed in a temperature range of from about $-10$ to 100 degrees centigrade and is preferably performed in a temperature range of from about 5 to 60 degrees centigrade, and more preferably at a temperature from about 20 to 40 degrees centigrade. No appreciable changes and increases in the temperature of the gas stream occur based on the reaction and aerosol formation, which would require a separate cooling of the gas mixture in view of the lengths and the inner diameters recited for the reaction path, and where the gas stream flows at a volume of about 30 liters per hour through the reaction path.

The gas mixture with the aerosol flows through the aerosol filter 5, where the droplets are deposited at the filter pores in the aerosol filter 5. Aerosol filters are schematically shown in the German Printed Patent Document DE-OS 3,716,350. Aerosol filters are further taught in U.S. Pat. No. 5,055,688 and in the article "Extended Potentials and Applications to the NDIR Photometer URAS 10E" by M. Ascherfeld et al., Journal "Technisches Messen—tm", Vol. 57 (1990), Issue 1, pages 11–17.

The gas mixture, the excessive water, and the deposited aerosol leave jointly the aerosol filter 5 through an exit pipe 15. In most cases, the gas and the liquid flow together out of the aerosol filter 5. The gas and the liquid then pass jointly through the phase separator 6, where the separation of gas from liquid is performed. The gases to be analyzed, which are in this case for example oxygen $O_2$ and sulfur dioxide $SO_2$, are separated from the liquids in the downstream following phase separator 6, where the gases are separated from the liquid, and where the liquid is transported through the outlet port 13 to be disposed of.

A commercially available system for condensate deposition and discharge is available from Mannesmann Hartmann & Braun, Frankfurt am Main, Federal Republic of Germany, and described in Listenblatt 10/23-1.22 entitled "Condensate Deposition and Discharge". The reference shows a measurement gas cooler corresponding to the phase separator 6 of FIG. 1.

The purified gases pass to the analyzers 8 and 9 via the suction pump 7.

The function of the phase separator 6 can also be performed by the aerosol filter 5, if a discharge port 11 is provided at the filter casing, where the liquid parts can be separated from the gas stream at the discharge port 11. In case the filter 5 is employed as a phase separator, then the liquid phase is pumped off with a pump similar to the pump 13 shown in FIG. 1.

The above recited commercially available system for condensate deposition and discharge available from Mannesmann Hartmann & Braun, Frankfurt am Main, Federal Republic of Germany, and described in Listenblatt 10/23-1.22 entitled "Condensate Deposition and Discharge" shows a condensate discharge port comparable to the outlet port 13.

The time the aerosol filter 5 can be used without requiring servicing is independent whether a separate phase separator 6 is used or not used, but instead is limited by dirt carried along with the gas stream, where the dirt covers the pores of the aerosol filter and then a cleaning of the aerosol filter is required. In general, aerosol filters are permeable to liquids. The aerosol filter can be constructed such that the fine droplets of the aerosol are deposited at the aerosol filter, are collected at the aerosol filter, and leave the filter as a liquid.

The analyzers can be a non-dispersive infrared photometer such as the instrument described for example in the article "Extended Potentials and Applications to the NDIR Photometer URAS 10E" by M. Ascherfeld et al., Journal "Technisches Messen—tm", Vol. 57 (1990) Issue 1, pages 11–17. A membrane condenser for measuring very small pneumatic alternating pressures is taught in the German Patent DE-3,640,718-C2 to Willi Apel et al. A commercially available analyzer is supplied by Mannesmann Hartmann & Braun, Frankfurt, Federal Republic of Germany, and shown in Listenblatt 10/20-1.14 entitled "Analyzers for IR-Absorbing Gases". Alternatively, a magnetomechanical oxygen analyzer can be employed such as the magnetomechanical oxygen analyzer MAGNOS3 supplied by Mannesmann Hartmann & Braun, Frankfurt, Federal Republic of Germany, and described in Listenblatt 21-1.21.

The gas mixture to be treated is composed of the components to be subjected to a measurement such as for example oxygen $O_2$ and sulfur dioxide $SO_2$ and of a carrier gas, which contains other gas components not of importance in the context of the present considerations. The gas mixture can be roast gas generated for example during the heating and roasting of ores under air access, smoke gases, burnt gas, exhaust gas, flue gas, furnace gas, fume gas, fumigating gas or smoke gases, as employed for a preservation of sausage products, as well as exhaust gases from special garbage incinerator plants. In general, the partial volume of the interfering component is less than 1 volume percent.

The following are examples for gas compositions:

| | |
|---|---|
| Roast gases for embodiment shown in FIG. 1: | |
| oxygen $O_2$ - measurement region: | 0 to 20 percent by volume |
| sulfur dioxide $SO_2$ - measurement region: | 0 to 20 percent by volume |
| sulfur trioxide $SO_3$ as interfering gas: | 0.1 percent by volume |
| Smoking gases: | |
| carbon monoxide CO - measurement region: | 0 to 1.5 percent by volume |

-continued

| | |
|---|---|
| oxygen O$_2$ - measurement region: | 16 to 21 percent by volume |
| tar as an interfering component: | 1 weight percent, given in weight percent, since the interfering component is already present as droplets |
| Exhaust gases: | |
| carbon monoxide CO - measurement region: | 0 to 1000 ppm (parts per million) |
| sulfur dioxide SO$_2$ - measurement region: | 0 to 100 ppm |
| oxygen O$_2$ - measurement region: | 0 to 20 percent by volume |
| nitrogen oxide NO$_x$ - measurement region: | 0 to 1000 ppm |
| interfering component hydrogen chloride HCl: | 0 to 3 volume percent |

It will be understood that each of the elements described above, or two or more together, may also find a useful application in other types of analytical system configurations and other methods and devices for gas processing differing from the types described above.

While the invention has been illustrated and described as embodied in the context of a method and a device for the treatment of a gas to be analyzed, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method for treatment of a gas mixture to be analyzed comprising
    sampling the gas mixture to provide a gas stream;
    mixing an additional reagent to the gas stream, wherein the reagent reacts with undesired components forming an aerosol;
    passing the gas stream after admixing of the reagent through a reaction tube, wherein the reaction tube provides a dwelling time sufficient for a generation of aerosols incorporating said undesired components;
    separating components of the gas mixture undesirable for an analytical procedure from the gas mixture with an aerosol filter.

2. The method according to claim 1, further comprising metering the reagent material continuously by feeding the reagent material through a metering device into the gas stream.

3. The method according to claim 1, further comprising metering the reagent material under pulsed feeding the reagent material through a metering device into the gas stream.

4. The method according to claim 1, wherein water is employed as the reagent material for an elimination of sulfur trioxide $SO_3$ from the gas stream, wherein the weight parts of water to weight parts of sulfur trioxide $SO_3$ are metered in a ratio of larger than 20 to 1.

5. The method according to claim 1, wherein solvents for tars are employed as reaction material for an elimination of tars from the gas stream.

6. The method according to claim 1, wherein the separation of the aerosol particles is performed in a phase separator connected to the aerosol filter.

7. The method according to claim 1, further comprising suctioning the gas stream after separating the aerosol particles into a gas analyzer;

analyzing the gas stream in the gas analyzer.

8. A method for treatment of a gas to be analyzed contained in a gas mixture, wherein components of the gas mixture undesirable for an analytical procedure are separated from the gas mixture under use of an aerosol filter, wherein a reagent is mixed to the gas stream, wherein the reagent forms with the undesired components an aerosol; and wherein the gas stream flows after admixing the reagent through a reaction path distance, wherein the reaction path distance provides a dwelling time for the generation of aerosols.

9. The method according to claim 8, wherein the reagent material (3) is continuously fed through a metering device (10) into the gas stream.

10. The method according to claim 8, wherein the reagent material is pulsed fed to the gas stream through a metering device.

11. The method according to claim 8, wherein water is employed as the reagent material for an elimination of sulfur trioxide $SO_3$ from the gas stream, wherein the weight parts of water to weight parts of sulfur trioxide $SO_3$ are metered in a ratio of larger than 20 to 1.

12. The method according to claim 8, wherein solvents for tars are employed as reaction material for an elimination of tars from the gas stream.

13. An apparatus for the treatment of a gas to be analyzed comprising a feed-in port for entering a gas sample stream including undesired components to be separated from the gas sample stream for allowing performing a gas analysis of the gas sample stream;

means connected to the feed-in port for adding reagent material to the gas sample stream;

a reaction tube having an input end and having an output end and connected to the feed-in port for reacting the gas sample and the reagent to form an aerosol, wherein the gas stream passes through the reaction tube over a reaction distance after feeding in the reagent material for providing a dwelling time for a generation of aerosols with the undesired components in the mixture of the gas sample stream and of the reagent material;

an aerosol filter having an input connected to the output of the reaction tube and having an output, wherein the aerosol filter is disposed downstream of the reaction tube, and wherein the aerosol filter separates the aerosols from the gas stream.

14. The apparatus according to claim 13, further comprising a discharge port disposed at the aerosol filter, wherein the discharge port allows using the aerosol filter as a phase separator.

15. The apparatus according to claim 13, further comprising a phase separator having an input connected to the output of the aerosol filter and having an output.

16. The apparatus according to claim 15, further comprising
- a suction pump having an intake connected to the output of the phase separator and having an output;
- a gas analyzer having an input connected to the output of the suction pump.

17. An apparatus for the treatment of a gas to be analyzed in a gas mixture, in particular where undesired components are to be separated from a gas mixture for performing an analysis comprising
- a feed-in port for entering a gas sample stream;
- means connected to the feed-in port for adding reagent material to the gas sample stream;
- a reaction tube having an input end and having an output end and connected to the feed-in port for reacting the gas sample and the reagent to form an aerosol, wherein the gas stream passes through the reaction tube (4) over a reaction distance after feeding in the reagent material (3), for providing a dwelling time for a generation of aerosols with the undesired components in the mixture of the gas sample stream and of the reagent material;
- an aerosol filter (5) having an input connected to the output of the reaction tube and having an output, wherein the aerosol filter (5) is disposed downstream of the reaction tube (4), and wherein the aerosol filter (5) separates the aerosols from the gas stream.

18. The apparatus according to claim 17, wherein the aerosol filter (5) is furnished with a discharge port (11), which discharge port (11) allows to use the aerosol filter (5) as a phase separator.

* * * * *